US006541267B1

(12) United States Patent
Halstead

(10) Patent No.: US 6,541,267 B1
(45) Date of Patent: *Apr. 1, 2003

(54) METHODS FOR TESTING OXIDATIVE STRESS

(75) Inventor: Bruce W. Halstead, Grand Terrace, CA (US)

(73) Assignee: Bio-Defense Nutritionals, Inc., Grand Terrace, CA (US)

( * ) Notice: Subject to any disclaimer, the term of this patent is extended or adjusted under 35 U.S.C. 154(b) by 86 days.

This patent is subject to a terminal disclaimer.

(21) Appl. No.: 09/704,448

(22) Filed: Nov. 1, 2000

Related U.S. Application Data

(63) Continuation-in-part of application No. 09/253,223, filed on Feb. 19, 1999, now Pat. No. 6,165,797.

(51) Int. Cl.$^7$ .................. G01N 21/78; G01N 33/493

(52) U.S. Cl. .................. 436/128; 436/166; 436/130; 436/808

(58) Field of Search ................. 436/128, 130, 436/166, 808, 56, 164, 169, 174, 175

(56) References Cited

U.S. PATENT DOCUMENTS 5,950,634 A * 9/1999 Ochi et al. .................. 128/898
6,165,797 A * 12/2000 Halstead .................... 436/128

* cited by examiner

*Primary Examiner*—Lyle A. Alexander
(74) *Attorney, Agent, or Firm*—Rutan & Tucker LLP; Robert D. Fish

(57) ABSTRACT

Method and compositions for determining oxidative stress in a subject are provided in which presence of an aldehyde in a biological fluid is correlated with an oxidative stress in a subject. A test reagent having a pH regulator, a reducing agent, and an aldehyde-reactive chromogen is mixed with the biological fluid, and the color of the resulting aldehyde-modified chromogen is correlated with the oxidative stress.

11 Claims, No Drawings

METHODS FOR TESTING OXIDATIVE STRESS

This is a continuation-in-part of allowed U.S. application Ser. No. 09/253,223, filed Feb. 19, 1999, now U.S. Pat. No. 6,165,797 which is incorporated by reference herein.

FIELD OF THE INVENTION

The field of the invention is detection and quantification of oxidative stress in a subject.

BACKGROUND

It is by now common knowledge that stress in mammalian subjects develops directly or indirectly into a display of oxygenated species, which tends to change the usually reduced state of the body to a hyperoxygenated state. This hyperoxygenated state includes generation and reaction of hydroxides, peroxides and free radical species, which are thought to be implicated in physiological imbalance and actual physical damage. Physical damage can produce pathological states, which for example, may lead to atherosclerotic plaques. Such plaques often result in the deposition of lipids and may further lead to blockage of arteries that can cause a cessation of blood flow to the heart with a resulting heart attack. This is one of many human disease states that are thought to be caused by free radical attack from the hyperoxygenated state caused by stress. Despite the relatively large body of information linking oxidative stress to various diseases and/or disease states, there is still an appreciable need for suitable markers and test systems to determine the level of oxidative stress in a simple and inexpensive manner.

Malondialdehyde is a component of normal urine, and its presence can be determined using relatively expensive and typically stationary equipment such as spectrophotometers, fluorometers, high performance liquid chromatographs and gas chromatograph mass spectrometers. Such equipment typically enables an operator to determine not only the quantity of a particular aldehyde, but also to determine the chemical nature of a particular molecule with an aldehyde function. Unfortunately, the operator of such equipment needs to be highly trained, and the weight and size of the equipment is generally prohibitive for point-of-care tests.

Alternatively, a broad spectrum of chemically distinct aldehydes may be detected by mixing a drop of sample solution (which may contain the aldehyde) with 2 ml of 72 percent sulfuric acid in a test tube (disclosed at page 395 in "Qualitative Analysis by Spot Tests", Third Edition, authored by F. Feigl and published by Elsevier Publishing Company, Inc.). A small amount of solid chromatropic acid (1,8-dihydroxynapthlanene-3,6-disulfate) is added to the mixture, and the test tube is heated in a 60° C. water bath for about ten minutes. If an aldehyde is present, a bright violet color appears in the test solution. While the test is relatively non-specific for a particular aldehyde, the sensitivity of the test is reportedly about 3 ppm. However, the reaction mixture typically requires vigorous heating for at least 10 minutes to provide an at least semi-quantitative and reliable test result.

In yet another method generally applicable to aldehydes, described at pages 339–340 of the Feigl publication, a drop of aqueous (or alcoholic) solution suspected of containing an aldehyde is treated on a spot plate with a drop of sulfurous acid and a drop of fuchsin/sulfuric acid and allowed to react on the plate. A red to blue color appears within about two to thirty minutes, according to the amount of aldehyde present in the test solution being tested. Such test is reportedly sensitive to about one microgram of formaldehyde in the drop of solution being tested. Although the fuchsin/sulfuric acid reaction can advantageously be performed at room temperature, the test results tend to vary depending on the time allowed for the reaction.

Although various quantitative and qualitative tests for aldehydes are known in the art, all or almost all of them suffer from one or more disadvantage. Moreover, despite the existence of known tests, it has never been appreciated that such tests can be applied to malondialdehyde in urine to detect oxidative stress. Thus, there is still a need to provide methods and apparatus for detecting oxidative stress in subjects.

SUMMARY OF THE INVENTION

It has been discovered that the oxidative stress state of a person can be measured from the release into the urine of an aldehyde, and particularly malondialdehyde, and that an aldehyde-reactive chromogen based calorimetric test can measure the released aldehyde in a rapid, easily performed test.

In particular, a method of determining oxidative stress in a subject has one step in which presence of an aldehyde in a biological fluid of a subject is correlated with an oxidative stress in the subject. In another step, a test reagent comprising a pH regulator, a reducing agent, and an aldehyde-reactive chromogen is provided, and the test reagent is combined with the biological fluid to produce an aldehyde-modified chromogen. In yet another step, a color of the aldehyde-modified chromogen is correlated with the oxidative stress.

In one aspect of the inventive subject matter, any biological fluid is considered suitable for use with the test, and especially preferred fluids include saliva, serum, plasma, and spinal fluid, most preferably urine. It is further contemplated that such fluids are derived from a mammalian system (e.g., human, live stock, pet, or cell culture).

In a further aspect of the inventive subject matter, the aldehyde comprises a dialdehyde, and especially contemplated dialdehydes include malondialdehyde. Particularly preferred pH regulators comprise a buffer or an acid, such as phosphoric acid and/or glacial acetic acid, and reducing agents typically have a sulfur (e.g., sodium metabisulfide) and/or phosphorous atom (e.g., TCEP). Further preferred aldehyde-reactive chromogens (e.g., fuchsin) include a reactive group that selectively reacts with an aldehyde and thereby shift their absorption maximum towards higher or lower wavelength in a concentration dependent manner.

DETAILED DESCRIPTION

A test kit for determination of oxidative stress in a subject generally comprises a test reagent with a pH regulator, a reducing agent, and an aldehyde-reactive chromogen, wherein the aldehyde-reactive chromogen in the test reagent reacts with an aldehyde from a biological fluid to form an aldehyde-modified chromogen, and wherein the aldehyde-modified chromogen has a color intensity that correlates with the oxidative stress in the subject.

Consequently, a method of determining oxidative stress in a subject has a step in which the presence of an aldehyde in a biological fluid of a subject is correlated with an oxidative stress in the subject. In another step, a test reagent comprising a pH regulator, a reducing agent, and an aldehyde-reactive chromogen is provided, and the test reagent is combined with the biological fluid to produce an aldehyde-modified chromogen. In a yet further step, a color of the aldehyde-modified chromogen is correlated with the oxidative stress.

In a particularly preferred aspect of the inventive subject matter, a testing solution or reagent for testing for the presence of aldehyde in an aqueous solution comprises a solution of acetic acid, preferably about 20% acetic acid, and two additional ingredients designated herein as "Ingredient A" and "Ingredient B". Ingredient A consists essentially of sodium metabisulfite, phosphoric acid, and deionized water. The preferred proportions of the elements of ingredient A are about 18–22 grams sodium metabisulfite, 9–11 ml of concentrated phosphoric acid, and about 450–550 ml deionized water. Most preferably, the proportions are 20 grams sodium metabisulfite, 10 ml phosphoric acid, and about 500 ml deionized water. Ingredient B consists essentially of a mixture of basic fuchsin (certified grade) and Ingredient A in the preferred proportions of about 0.45–0.55 grams basic fuchsin in about 90–110 ml of Ingredient A. Most preferably, the proportions are about 0.50 grams of basic fuchsin in about 100 ml of Ingredient A.

The components of the reagent are mixed in the proportion of about 90 to 110 parts of 20% acetic acid, 13.5–16.5 parts Ingredient A, and about 4.5–5.5 parts Ingredient B. An alternative method of making the reagent is as follows. First, dissolve 4 grams of sodium metabisulfite in 80 ml of deionized water. Then, add 2 ml of concentrated phosphoric acid, and dilute the mixture with a quantity of deionized water sufficient to make 100 ml of dilute mixture. Then add 0.5 gram of basic fuchsin, and about 10 grams of bone charcoal to decolorize the mixture. Remove the charcoal by centrifuging and filtering the mixture. Then, to 100 ml of the decolorized solution, add 100 ml of 20%–40% glacial acetic acid, and finally, add 100 ml of deionized water. The active components are present in the reagent made this way in about the same proportion as in the method previously described.

The testing solution described above is preferably stored in individual, sealed test-size ampoules or vials of conventional medical solution type. When packaged in such a manner and stored in a cool, dry place, the sealed bottles or vials have an expected shelf storage life of at least 12 months. Assurance of active testing solution may be achieved, as described below, by positive aldehyde test procedures.

A test for the presence of malondialdehyde in an aqueous solution is then made by mixing about 1 ml of test solution (containing traces of aldehyde) into about 0.2–0.6 ml of testing solution formulated as above. If the mixture of the test sample and testing solution remains colorless after a waiting period of about 2–5 minutes, the test is negative and the test sample therefore contains less than about 2 ppm aldehyde. Any color change of the mixture indicates presence of aldehyde in the test solution in a concentration greater than about 2 ppm. A positive malondialdehyde test is preferably by quality control techniques made before testing the test samples to assure that the testing solution is properly formulated or that, for example, the reagent bottles have not been replaced with other bottles containing non-testing solutions.

The positive malondialdehyde test is preferably performed by injecting 1 ml of available "Positive Aldehyde Test Solution (Standard)" into a bottle containing about 0.2–0.6 ml of the test solution. In approximately 2–5 minutes, the solution in the bottle should develop a pinkish-purple color provided the bottle contains properly formulated aldehyde testing solution. Otherwise, the bottle of "testing solution" from which the test bottle was selected should be discarded. The above-described positive test for aldehyde is sensitive to 10 ppm or more of aldehyde. For a 5 ppm, a positive test for aldehyde, 0.5 ml of deionized water is used. A color less intense than that of the 10 ppm aldehyde test is obtained for the 5 ppm aldehyde test.

Basic fuchsin is a purple powder which reacts with aldehydes in the skin, urine or blood plasma. With low or no aldehydes present, there is no color development. With moderate or high levels of aldehydes, color gradations are roughly dependent on the level of aldehydes present. The amino group of the fuchsin couples with the aldehyde to produce the pink to purple color approximately dependent on the amount of aldehyde present in the blood or urine. A 40% glacial acetic acid solution gives maximum color development for the fuchsin reaction. Sodium metabisulfite ties up free oxygen so that only the aldehydes react with the fuchsin group. Basic fuchsin changes color in an acidic solution, relative to the amount of aldehyde present in the urine samples. The color developed depends on the pH, which is controlled by the amount of acid present. Metabisulfite is used to stop the interference of oxygen from air. Establishing a nitrogen blanket over the reagent mixture gives greater shelf life of the reagent to stop any oxygen reaction with the reagent. The phosphoric acid stabilizes the pH in a rough adjustment and the acetic acid gives the fine acid pH stabilization.

In alternative aspects of the inventive subject matter, it should be appreciated that the order, composition, and relative molar ratios of the reagents may vary substantially, and numerous modifications are contemplated so long as the test reagent comprises a pH regulator, a reducing agent (which may even be optional), and an aldehyde-reactive chromogen.

For example, the pH regulator need not necessarily be limited to phosphoric acid and glacial acetic acid, and alternative pH regulators may include a buffer, an organic, an inorganic acid, or any reasonable combination thereof. For example, depending on the desired pH or pH range, suitable pH regulators may include a glycin-HCL buffer, a citrate buffer, a phosphate buffer, an acetate buffer, etc., and appropriate acids may include nitric acid, sulfuric acid, hydrochloric acid, and so forth. Still further, it should be appreciated that where the reaction between the aldehyde and the aldehyde-reactive chromogen is base-facilitated or base-catalyzed, organic or inorganic bases may be employed, and contemplated bases include sodium hydroxide, potassium hydroxide, deprotonated weak organic acids, and any reasonable combination thereof.

With respect to the reducing agent, it is contemplated that many alternative reducing agents are also appropriate, and alternative reducing agents include agents with a sulfur and/or phosphorous atom. For example, where cost effectiveness is especially desirable mercaptoethanol, dithioerythrol (DTE) or dithiothreitol (DTT) may be utilized. On the other hand, where the objectionable odor of sulfur-based reagents is to be circumvented, phosphorous based reducing agents such as tris(2-carboxyethyl)phosphine (TCEP) may be employed. While the use of a reducing agent is generally preferred, it is also contemplated that no reducing agent may be necessary at all, especially where the remaining reagents/fluids have been purged (e.g., with argon) and/or have been kept under nitrogen or other oxygen free atmosphere.

In yet further contemplated aspects, the aldehyde-reactive chromogen need not be limited to fuchsin, and various alternative aldehyde-reactive chromogens are contemplated. It is generally contemplated that suitable aldehyde-reactive chromogens comprise an aromatic system which may further be conjugated with at least another double- or triple bond containing system, and it is especially preferred that such aldehyde-reactive chromogens will have an absortion maximum of between about 240 nm to approximately 900 nm. With respect to the molar extinction coefficient, it is generally preferred that the molar extinction coefficient if the aldehyde-modified chromogen is between 100–100000, more preferably between 1000 and 50000, and most preferably between 10000 and 35000. It is further contemplated that suitable aldehyde-reactive chromogens have at least one reactive group that specifically reacts with an aldehyde, and particularly contemplated reactive groups include nucleophilic groups such as =NH, —NH$_2$, —SH, —OH, etc. Suitable aldehyde-reactive chromogens are contemplated to have an absorption maximum and a reactive group that selectively reacts with the aldehyde, wherein the absorption maximum exhibits a hyperchromatic or hypochromatic shift when the reactive group reacts with the aldehyde. Alternatively, the maximum may be unaffected by the reaction of the reactive group, and it is then contemplated that the aldehyde-modified chromogen has (or looses) an additional maximum when compared to the aldehyde-reactive chromogen.

It is generally contemplated that the concentration of aldehyde-modified chromogen can be visually (i.e., in an non-automated manner) determined, for example, by employing a reference chart which may be part of a test kit. Contemplated reference charts may thereby include a relative or arbitrary readout, or a semi-quantitative or quantitative readout. Alternatively, it is contemplated that the determination of the aldehyde may include an at least partially automated routine, and particularly contemplated routines may include a spectrophotometer (single or multiple wave length).

With respect to molar proportions of alternative components, it should be appreciated that a particular composition will typically dictate particular molar proportions of the components, however, only such molar proportions are contemplated that will result in an observable and/or quantifiable change in light absorption (typically UV/VIS) when the aldehyde-reactive chromogen reacts with the aldehyde. While it is generally contemplated that the change in absorption has a substantially linear dependence on the concentration of the aldehyde-modified chromogen (i.e., follows the Lambert-Beer law), non-linear dependence is also contemplated. For example, where the aldehyde generates a catalytic intermediate species, logarithmic or pseudo-logarithmic dependence may occur.

It is generally contemplated that malondialdehyde (MDA) and other related aldehydes are released from the breakdown of long chain polyunsaturated fatty acids by free radical attack. Interestingly, high levels of MDA and related aldehydes are found in a variety of diseases and disease states other than oxidative stress. Therefore, it should be especially appreciated that the methods and compositions according to the inventive subject matter may also be useful in detecting and/or confirming abnormal metabolism states, including coronary artery disease, type-1 and type-2 diabetes, and Parkinson disease.

Thus, specific embodiments and applications of tests for oxidative stress have been disclosed. It should be apparent, however, to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

What is claimed is:

1. A method of determining oxidative stress in a subject, comprising:

correlating a presence of an aldehyde in urine of a subject with an oxidative stress in the subject;

providing a test reagent comprising a pH regulator, a reducing agent, and an aldehyde-reactive chromogen, wherein the reducing agent includes at least one of a sulfur atom and a phosphor atom;

combining the test reagent with the urine to produce an aldehyde-modified chromogen; and correlating a color of the aldehyde-modified chromogen with the oxidative stress.

2. The method of claim 1 wherein the pH regulator comprises a buffer.

3. The method of claim 1 wherein the reducing agent comprises sodium metabisulfide.

4. The method of claim 1 wherein the aldehyde-reactive chromogen has an absorption maximum and comprises a reactive group that selectively reacts with the aldehyde, and wherein the absorption maximum exhibits a hypochromatic shift when the reactive group reacts with the aldehyde.

5. The method of claim 1 wherein the aldehyde-reactive chromogen comprises fuchsin.

6. The method of claim 1 further comprising automatically determining the color of the aldehyde-modified chromogen with a spectrophotometer.

7. The method of claim 1 wherein the subject is a human.

8. The method of claim 1 wherein the aldehyde comprises a dialdehyde.

9. The method of claim 8 wherein the dialdehyde is a malondialdehyde.

10. The method of claim 1 wherein the pH regulator comprises an acid.

11. The method of claim 10 wherein the acid comprises at least one of a phosphoric acid and a glacial acetic acid.

* * * * *